United States Patent [19]
Simmons et al.

[11] Patent Number: 5,701,904
[45] Date of Patent: Dec. 30, 1997

[54] TELEMEDICINE INSTRUMENTATION PACK

[75] Inventors: Scott C. Simmons, Houston; John R. Pohl, Friendswood; Terrell M. Guess; Douglas A. Rushing, both of Houston, all of Tex.; Michael P. Caputo, Jr., Hanover, N.H.; Roger D. Billica, Houston, Tex.

[73] Assignee: Krug International, Houston, Tex.

[21] Appl. No.: 584,820

[22] Filed: Jan. 11, 1996

[51] Int. Cl.[6] ........................................ A61B 5/02
[52] U.S. Cl. .................. 128/670; 128/630; 128/746; 128/745; 128/715
[58] Field of Search .......................... 128/630, 637, 128/638, 670, 671, 672, 687–689, 731–733, 739–741, 746, 748, 715, 772, 773; 600/109, 110, 112

[56] References Cited

U.S. PATENT DOCUMENTS

| | | | |
|---|---|---|---|
| 3,903,871 | 9/1975 | Chisum et al. | 128/676 |
| 4,567,881 | 2/1986 | Heller | 128/746 |
| 4,878,501 | 11/1989 | Shue | 128/715 |
| 5,325,863 | 7/1994 | Pompei | 128/736 |
| 5,327,884 | 7/1994 | Hardy et al. | 128/736 |
| 5,363,839 | 11/1994 | Lankford | 600/112 |
| 5,419,312 | 5/1995 | Arenberg et al. | 128/736 |
| 5,441,047 | 8/1995 | David et al. | 128/670 |
| 5,462,051 | 10/1995 | Oka et al. | 128/630 |
| 5,527,261 | 6/1996 | Monroe et al. | 600/109 |
| 5,599,276 | 2/1997 | Hauptli et al. | 600/112 |

*Primary Examiner*—Jennifer Bahr
*Assistant Examiner*—Stephen Huang
*Attorney, Agent, or Firm*—Jacox, Meckstroth & Jenkins

[57] ABSTRACT

The invention concerns a portable medical diagnostic apparatus which includes three types of data-gathering instruments: (1) visual instruments (eg, otoscope, ophthalmoscope, rhino-laryngoscope, macro lens and fundus camera); (2) an audio instrument (eg, electronic stethoscope); and (3) data-gathering instruments (eg, pulse oximeter and ECG monitor). A video camera generates signals, based on images taken from the visual instruments. Other electronic circuitry generates signals based on output of the audio instrument and data-gathering instruments. The signals are transmitted to a remote site for analysis by medical personnel.

13 Claims, 10 Drawing Sheets

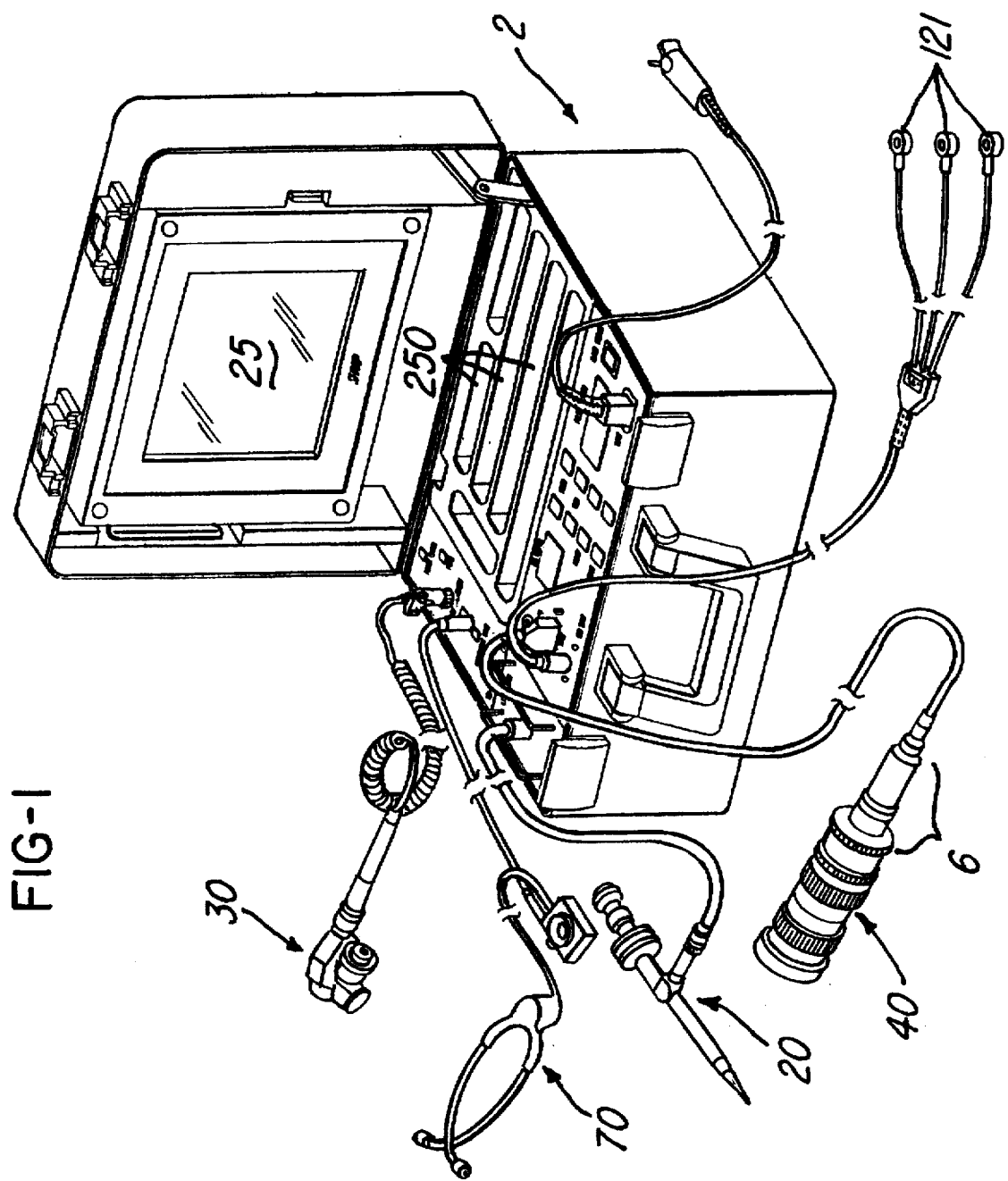

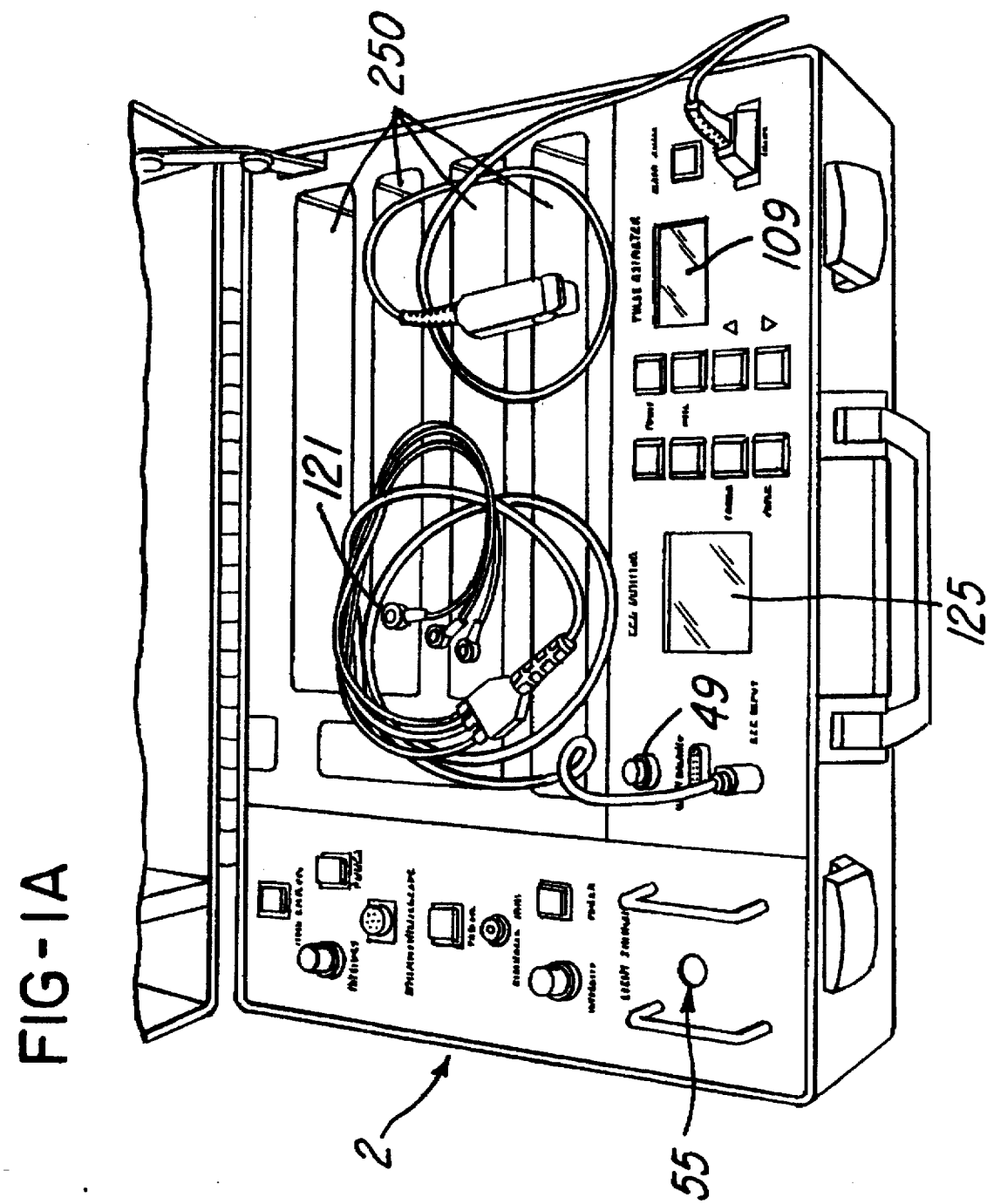
FIG-IA

TELEMEDICINE INSTRUMENTATION PACK

The invention relates to a portable medical diagnostic apparatus which contains (a) medical instruments for examining a subject, together with (b) a communication system for transmitting the data obtained to a remote site.

BACKGROUND OF THE INVENTION

Numerous situations arise where a basic medical examination of a subject is desired, but where medical personnel are not always available. Some examples are the following:

1. Space Exploration. The U.S. spacecraft known as the "Space Shuttle" carries a multi-person crew, but inclusion of a physician is not always feasible. However, situations can arise where a medical examination of a crew member is desirable.

2. Military Medicine. Military exercises and operations frequently occur in remote locations, where medical facilities are scarce or nonexistent.

3. Medically Under-served Areas. The number of fully staffed and equipped medical clinics in the world is relatively small, compared to the population and geographic area to be served. Frequently, a medical examination of a distant patient is desirable.

4. Emergency and Occupational Medicine. Industrial mishaps and natural disasters sometimes occur at locations where medical facilities are not available. Further, even if such a facility is nearby, the extent of damage can over-tax this facility and require assistance of a more remote facility.

5. Home Health Care. Many people recover from illness or accident in their homes, where physicians and a nursing staff are not generally available.

OBJECTS OF THE INVENTION

An object of the invention is to provide an improved medical diagnostic apparatus.

A further object of the invention is to provide a medical diagnostic apparatus which contains instruments by which a technician can perform a physical examination of a subject, and the apparatus contains a communication system that transmits results of the examination to a remote location for analysis by medical personnel.

Another object of the invention is to provide apparatus for conducting physical examinations involving observation (looking), auscultation (listening), and palpation (feeling/touching). The apparatus of the invention provides a method for physicians to remotely observe the ear, eye, skin, nose, throat, electrical activity of the heart (ECG), blood pressure, temperature, blood $O_2$ saturation (pulse oximeter), and remotely listen to the patients voice response to questions, heart, lung, and abdominal sounds.

SUMMARY OF THE INVENTION

In one form of the invention, medical instrumentation is applied to a subject, and takes visual images of organs such as the internal eye, external eye, skin, internal ear, external ear and internal body organs, and transmits these images to a remote location for medical personnel to view.

In another form of the invention, other instrumentation takes acoustic data, as from a stethoscope, and electronic data, as from a pulse oximeter and an ECG monitor. This other data is also transmitted remotely, for display to the medical personnel.

BRIEF DESCRIPTION OF THE DRAWINGS

FIG. 1 illustrates one form of the invention and shows a portable case or valise which carries certain medical instruments as also shown;

FIG. 1A is a view of the control panel of the valise shown in FIG. 1;

DETAILED DESCRIPTION OF THE INVENTION

FIG. 1 is a view of one form of the invention, and shows a valise 2 which is adapted to contain various medical instruments for use in examining a subject. The components shown in FIG. 1 will be explained with reference to FIGS. 2-7.

Video Imaging System

Figure 2:
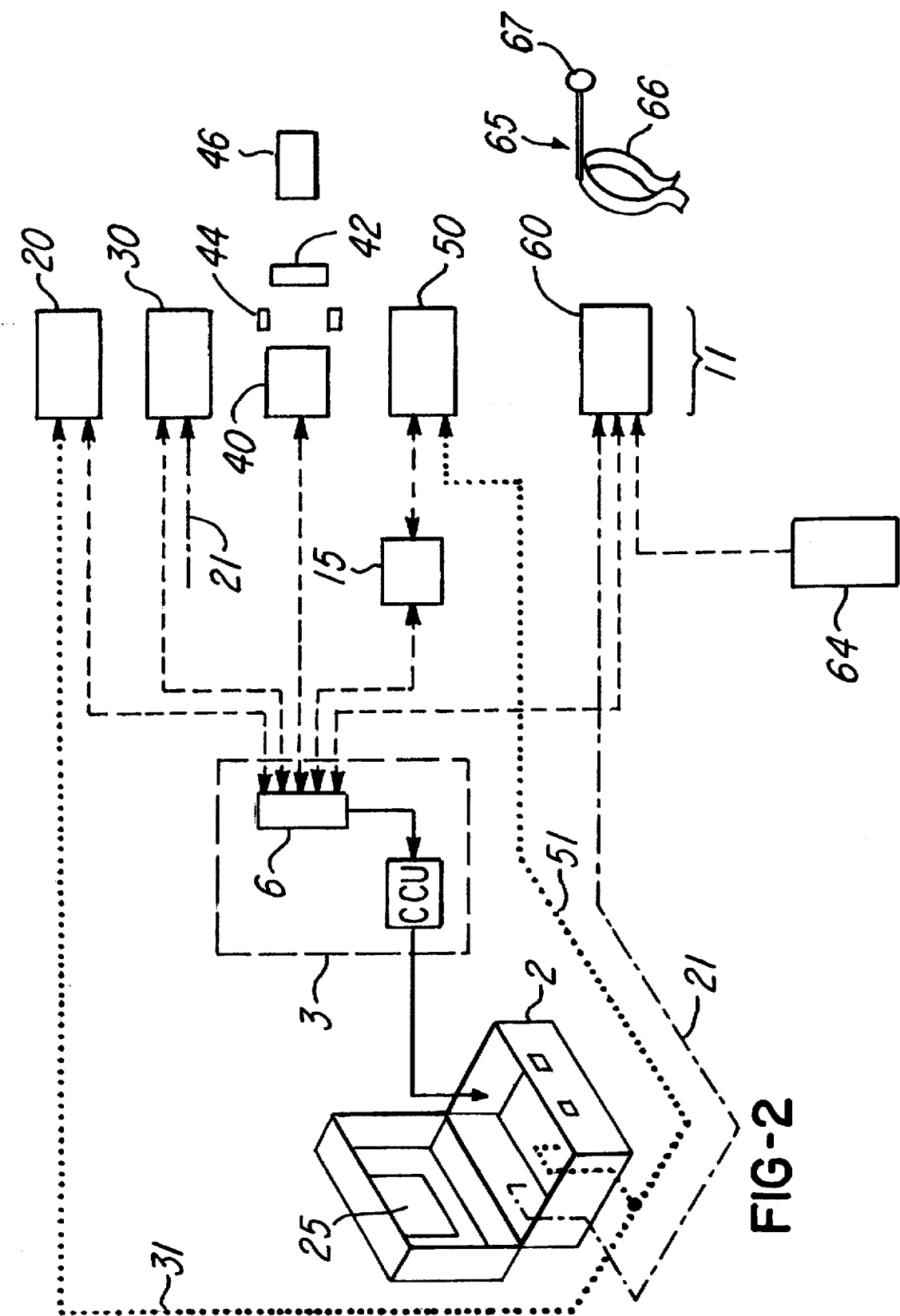
FIG. 2 is an exploded schematic of a video sub-system embodied by the invention.
Figure 3:
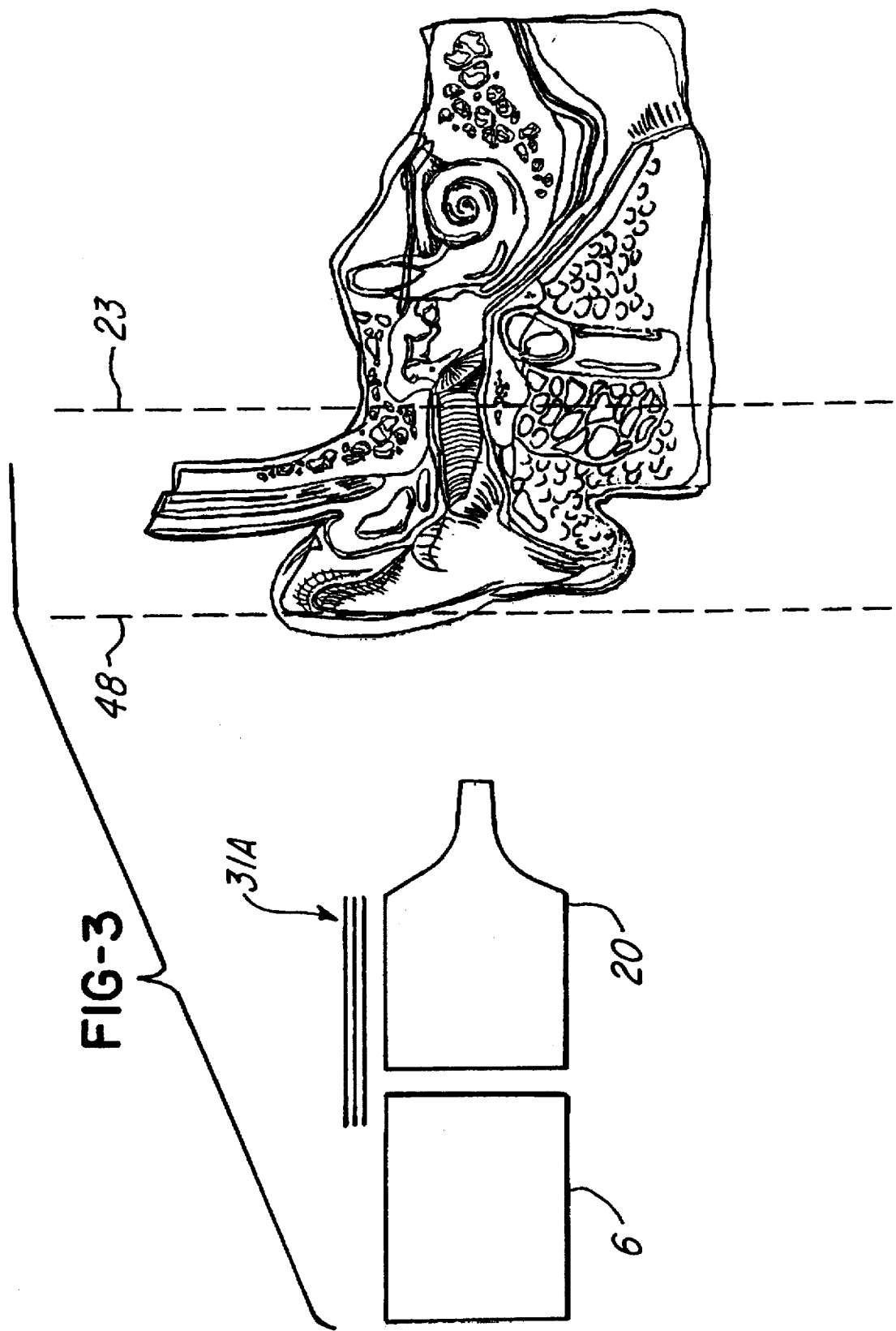
FIG. 3 illustrates operation of an otoscope 20, which is part of the video sub-system.

A valise 2 carries a video camera 3, shown in FIG. 2, a part of which is shown in FIG. 1. The video camera 3 is a commercially available Charge-Coupled Device (CCD) camera, in which the light-sensitive imaging head 6 (shown in FIG. 1) is separate from the camera control unit (CCU), in FIG. 2. The CCU contains electronics which scan the CCD array contained in the imaging head 6, and produce the electronic signals representing the image viewed. Such apparatus is commonly called a "remote head" camera.

One reason for separating the remote imaging head 6 from the CCU is to allow the more massive CCU to remain stationary, while the more lightweight imaging head 6 is manipulated by a technician. As will be explained shortly, one of several medical instruments is affixed to the imaging head 6. The light weight of the imaging head (in the range of 1.75 ounces) does not appreciably affect the manipulability of the instruments.

Accuracy in color rendition can be important in many situations of imaging a patient. The valise 2 is equipped with a white reference 46, shown in FIG. 2, for use in adjusting color response of the video camera. A technician images the white reference 46 using the video camera, and adjusts a white balance control 49, shown in FIG. 1A, until the image shown on the display 25 in FIG. 2 produces acceptable color. White references are known in the art.

Otoscope

Figure 4:
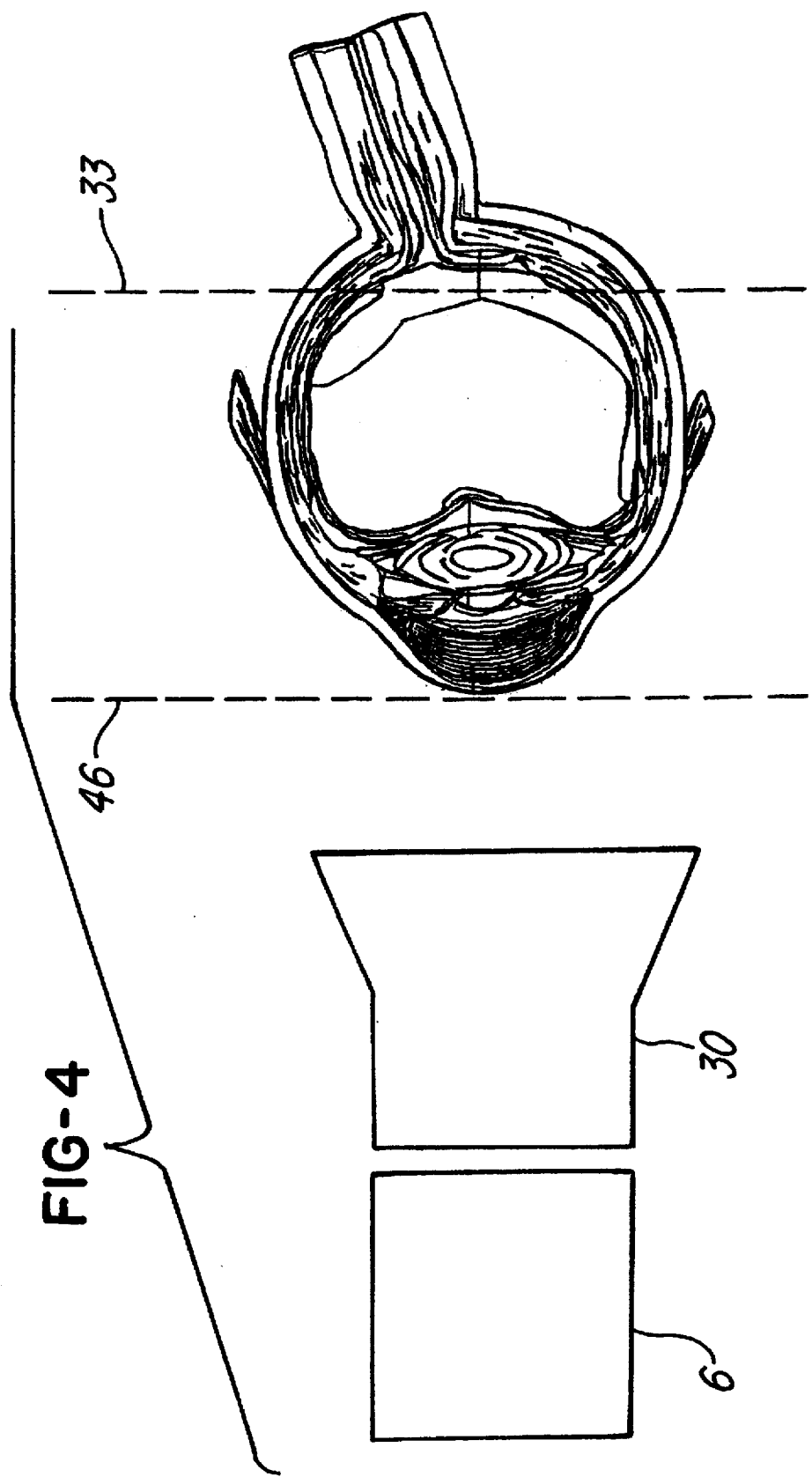
FIG. 4 illustrates operation of an ophthalmoscope 30, which is part of the video sub-system.

The imaging head 6 in FIG. 2 can be attached to one of several medical instruments which are shown in column 11 of FIG. 2: One instrument is a video otoscope 20 which allows imaging of the ear canal and tympanic membrane, such as at imaging plane 23 in FIG. 3. The otoscope is illuminated by a fiber optic cable 31 in FIG. 2, which receives light from a light source within the valise 2, indicated as 55 in FIG. 1A, and delivers light to the imaging plane 33 in FIG. 4 by a suitable arrangement of the exit ends 31A of the optic fibers, as indicated in FIG. 4.

The video camera 3 in FIG. 2 produces an image which is displayed on a display 25. The display is a commercially available Thin-Film Transistor (TFT) flat-panel display. In addition, the video camera 3 produces an analog signal which conforms to the NTSC standard (NTSC: National Television Standards Committee). This analog signal is delivered to a jack on the valise 2, for transmission to a remote location, as will be explained in connection with FIGS. 7 and 8.

One purpose of the display 25 is to provide feedback to the technician who is using the video camera in examining the subject. The display shows the image which the camera sees and also indicates the image which will be seen by the remote parties to whom the invention sends the video images taken.

Ophthalmoscope

A second instrument is a standard ophthalmoscope 30 shown in FIG. 2. This instrument allows imaging of the internal eye, such as at imaging plane 33 in FIG. 4. The opthalmoscope utilizes its own, standard illumination system which receives power through line 21 in FIG. 2, from a power supply (not shown) contained within the valise.

Macro Lens

A third instrument is a standard macro lens 40 shown in FIG. 2. The instrument has additional accessories such as a close-up lens 42 and a light ring 44. The macro lens 40 takes the form of a commercially available zoom lens having a field of view ranging from 1 to 100 square centimeters and an aperture ranging from F 1.8 to F 16.0.

The macro lens 40 is used for imaging the skin and superficial aspects of the physiology. For example, the macro lens can image the eye externally, at image plane 46 in FIG. 4. As another example, the macro lens can image the external ear, at image plane 48 in FIG. 3. As a third example, the macro lens can view the face or other parts of the physiology.

The light ring 44 in FIG. 2 can take the form of a standard ring illuminator, available from photographic supply houses. Alternately, the light ring can take the form of a ring of optic fibers, illuminated by the same light source which illuminates the otoscope 20.

Rhino-Laryngoscope

Figure 5:
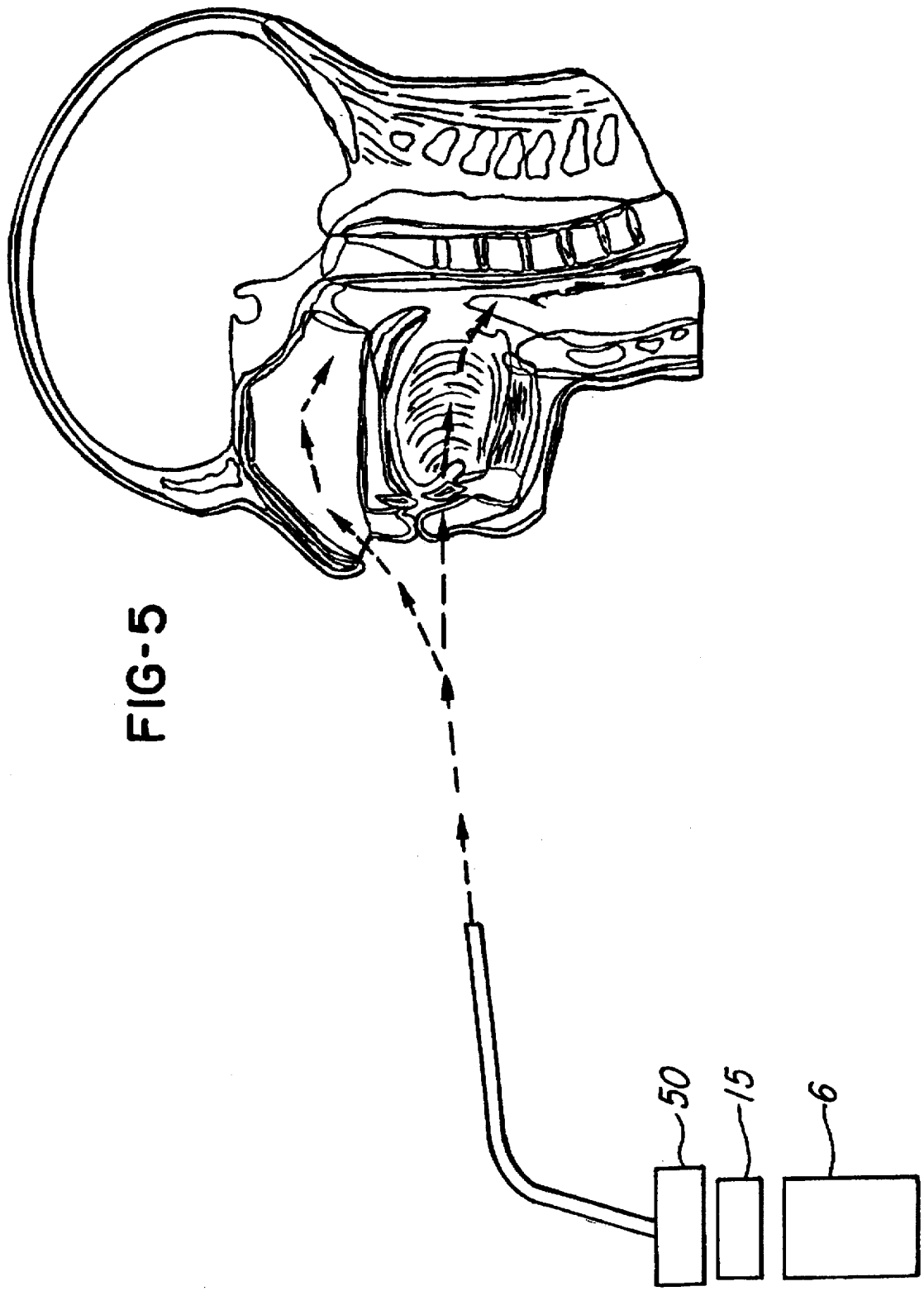
FIG. 5 illustrates operation of a rhino-laryngoscope which is part of the video sub-system.

A fourth instrument is a rhino-laryngoscope 50 shown in FIG. 2. This instrument is an endoscope used to view internal organs of the physiology, such as the throat, as indicated in FIG. 5. The rhino-laryngoscope 50 attaches to the remote imaging head 6 in FIG. 2 by mounting adapter 15, and is illuminated by a fiber-optic cable 51, and the cable is illuminated by the same light source which illuminates the fiber optic cable used for the ophthalmoscope. FIG. 1A illustrates the receptacle 55 into which a fiber optic cable is inserted for the respective instruments 30 and 50.

Fundus Camera

A fifth instrument is a fundus camera 60 shown in FIG. 2. This camera is used to image the fundus of the eye where the retina is located. A commercially available fundus camera is used, and the camera is ordinarily affixed to the camera back 64 of a 35 mm camera. The invention replaces the camera back 64 with the mounting adapter 15D which mounts the fundus camera to the imaging head 6, rather than to the camera back 64.

The most common use of the fundus camera is to view the retina near the plane 33 in FIG. 4. The fundus camera is not shown in FIG. 4, but would be located approximately in the position of the ophthalmoscope 30. The fundus camera 60 may also be used by withdrawing the fundus camera from the eye and changing the focus, thereby allowing the fundus camera to view the external eye, at image plane 46.

The fundus camera adapter 15D in FIG. 2 contains a 10 mm C-mount spacer and an achromatic lens, for viewing the fundus. In addition, to view the external eye, a 5 mm spacer can be added, for increased magnification.

Another type of spacer 65 is shown in FIG. 2. This spacer clips to the fundus camera by means of a spring clip 66. The spacer 65 contains a soft, pliant bulb 67 at its end, which contacts the subject's forehead. The spacer prevents accidental contact between the fundus camera and the eye itself. The 35 mm camera back 64 is optional, as indicated, and may be included within the valise 2, if desired.

Mode of Illumination

In the most general case, it is not critical whether a given instrument is illuminated by (a) electric power supplied by a power supply within the valise 2, which powers the instrument's own lamp or (b) a fiber optic cable, illuminated by a light source within the valise.

Display of Images

As stated above, the video camera 3 allows the images taken by the instruments shown in FIG. 2 to be displayed on the video display 25. The display presents the image seen by the video camera 3, such as the retina of the eye imaged by the ophthalmoscope 30. A significant feature of the imaging sub-system is that, in general, the image presented on the display 25 will be magnified, compared with the actual size of the physical object viewed.

Audio System

Figure 6:
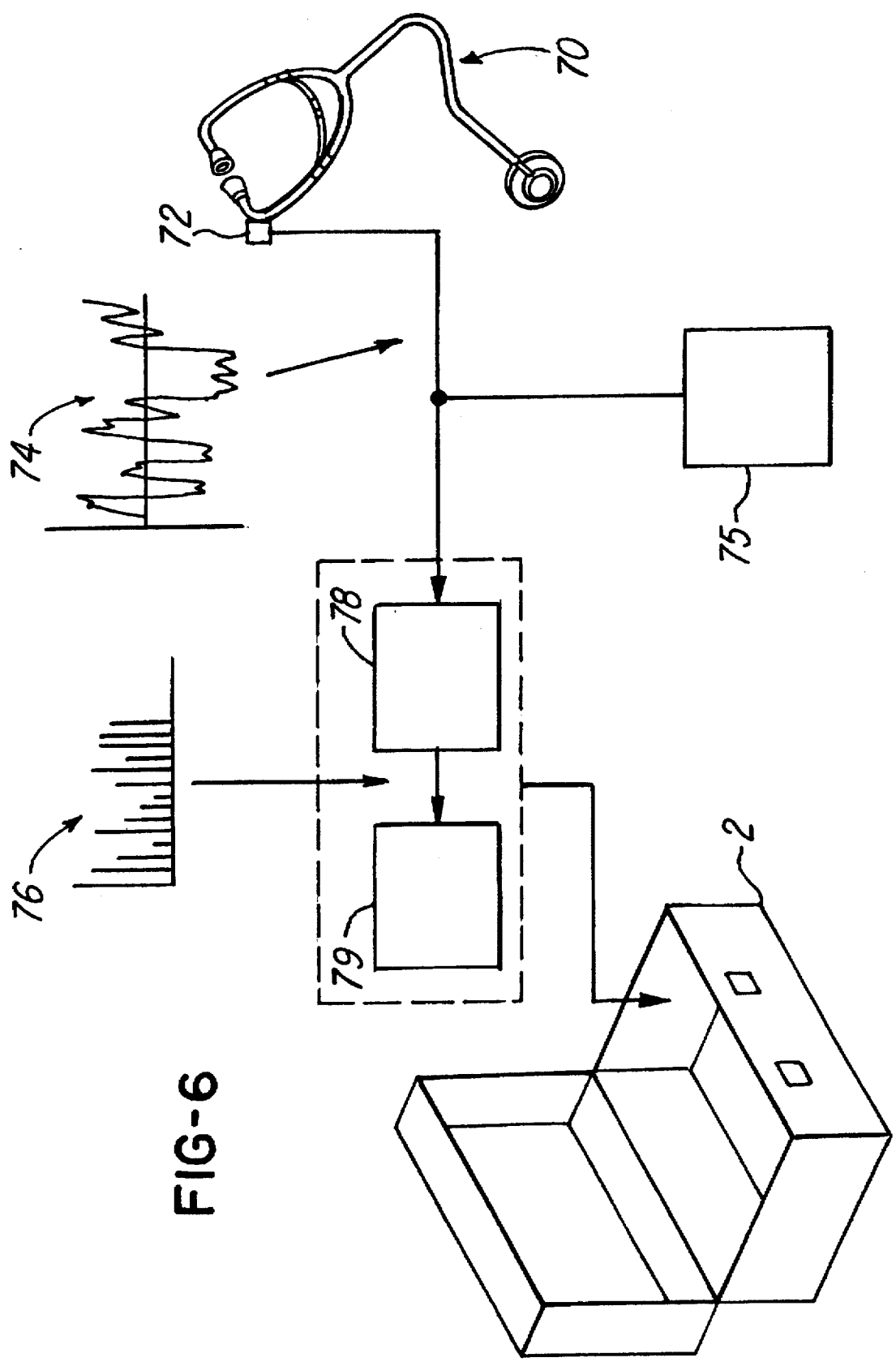
FIG. 6 illustrates an audio sub-system embodied by the invention and which includes an electronic stethoscope.

The valise 2 contains an electronic stethoscope 70, shown in FIGS. 1 and 6. The stethoscope is equipped with a piezoelectric crystal microphone 72 which produces an analog signal 74. As indicated by block 75, this signal can be conducted directly to an output jack mounted on the valise 2 for transmission to a remote site.

Alternately, the analog signal 74 can be converted to a digital signal 76 by Analog-to-Digital converter (A/D) 78. The digitized signal 76 is either stored internally, or transmitted by telephone modem, as indicated by block 79.

Two reasons for digitizing the stethoscope signal are the following. One is that the common-carrier telephone system is limited in bandwidth, from about 300 Hz to 3,000 Hz. However, audio signals produced by the human physiology, such as by the heart, lung, and intestinal system, which are detected by the stethoscope 70, can range in frequency from about 20 Hz to 1,500 Hz.

This frequency range exceeds the bandwidth of the common-carrier telephone system. Digitizing the analog signal allows transmission over the common-carrier telephone system, without loss of information (although the time required for transmission increases). A standard modem can be used. Digitizing of analog signals is known in the art.

A second reason is that storage of digital signals is quite simple, using modern computers. Use of a computer will be discussed below.

Data Sub-System

Figure 7:
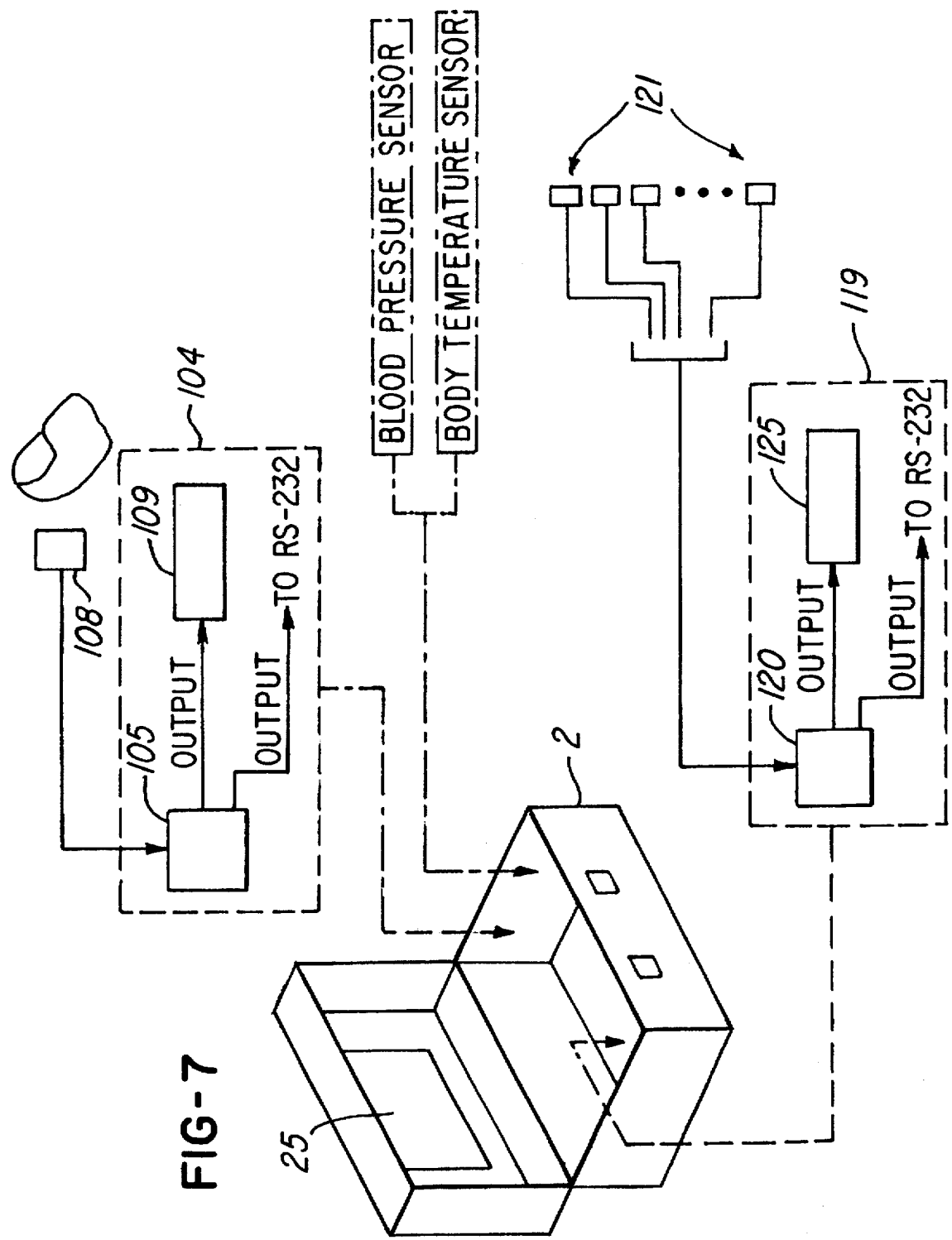
FIG. 7 illustrates a data subsystem embodied by the invention.

FIG. 7 illustrates two components of the data sub-system implemented by the invention. The first component is a pulse oximeter 104 which includes a finger probe 108 and processing electronics 105. The pulse oximeter 104 measures the oxygen saturation percentage (ie, SpO2) within the subject's bloodstream, as well as heart rate. The output is visually displayed on a Liquid Crystal Display (LCD) 109, also shown in FIG. 1A, and also made available in digital form to a serial RS-232 connector, as indicated.

The second component of the data sub-system shown in FIG. 7 is an ElectroCardio-Gram (ECG) monitor 119 which includes ECG leads 121. The ECG monitor 119 receives data from the leads 121 which are placed in contact with the subject. As with the pulse oximeter, the data is visually displayed on an LCD display 125, also shown in FIG. 1A, and presented to a second serial RS 232 output port, as indicated.

Two additional components can be added to those discussed in FIG. 7. One is a blood pressure sensor BP, which takes blood pressure of a subject, and produces digital data indicative of the pressure. The second is a body temperature sensor, TEMP, which takes body temperature of the subject, digitizes the temperature, and produces digital data indicative of the temperature. The digital output of both these components is fed to the serial output connector 106 in FIG. 8, or otherwise processed in an appropriate manner. Such blood pressure sensors and body temperature sensors are commercially available.

Design Architecture of Two Forms of Invention

First Architecture

Figure 8:
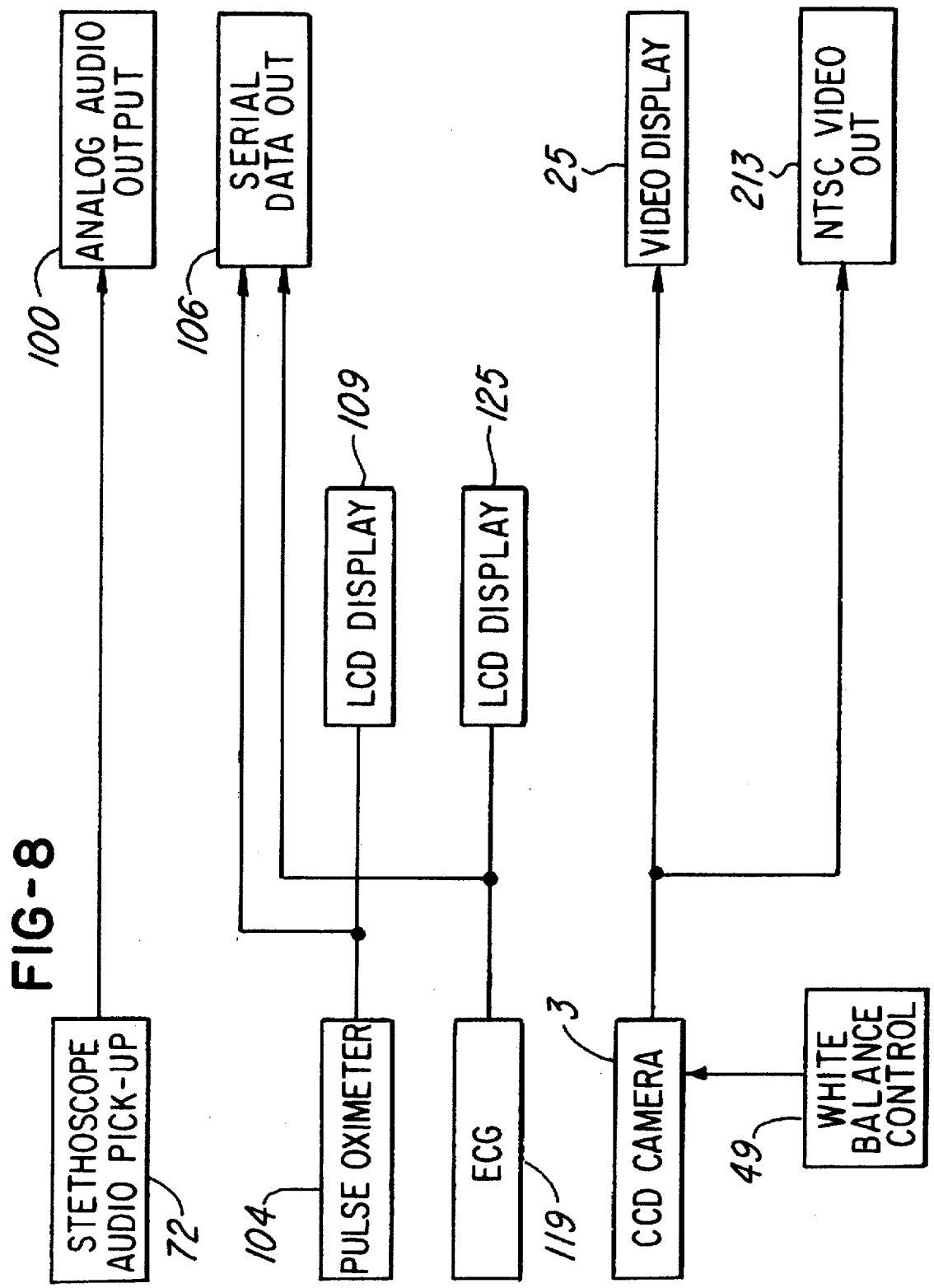
FIG. 8 illustrates an architecture of one form of the invention.

FIG. 8 illustrates an architecture of one form of the invention. The stethoscope audio pick-up 72, also shown in FIG. 6, delivers an audio signal to an analog output connector 100. (Intervening electronics, if used, are not shown for simplicity.) The pulse oximeter 104 and ECG monitor 119, also shown in FIG. 7, deliver their signals to two serial data output connectors 104. Also, their signals are displayed visually on respective LCD displays 109 and 125.

The CCD camera 3, also shown in FIG. 2, produces the image which it views on the video display 25, also shown in FIG. 2. In addition, the CCD camera's NTSC analog signal is presented directly to a jack 213, such as a standard BNC connector.

All of the equipment shown in FIG. 8 is packaged within the valise 2 of FIG. 1. The connectors 100, 106, and 213 are used by associated equipment to transmit data to a remote location.

Second Architecture

Figure 9:
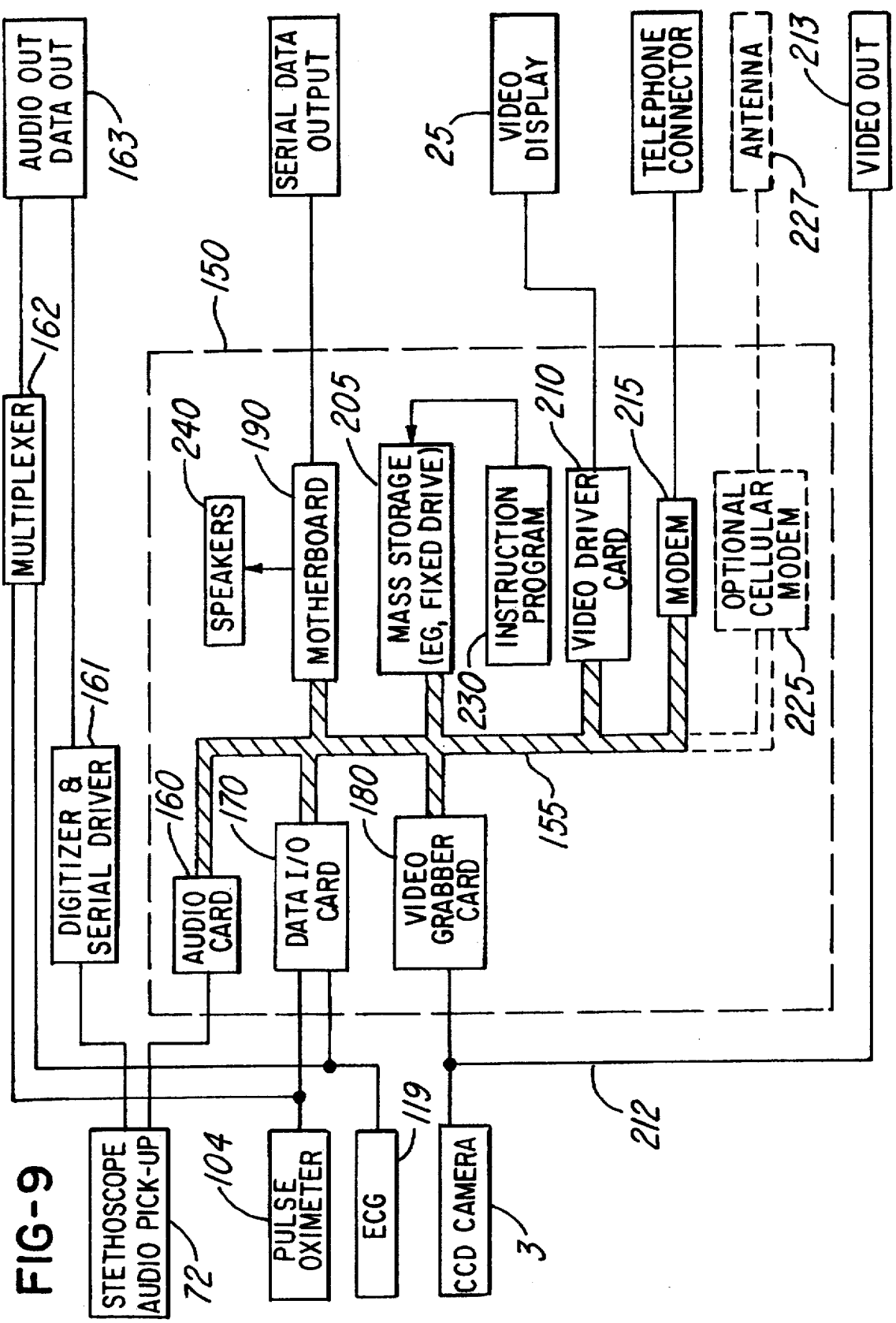
FIG. 9 illustrates an architecture of another form of the invention.

FIG. 9 illustrates an architecture of another form of the invention. All of the equipment identified in FIG. 9 is packaged within the valise 2 of FIG. 1.

The invention includes a computer 150, which can take the form of a single-board computer conforming to the AT/XT architecture, developed by IBM corporation, Armonk, N.Y., which is based on the 8XX86 microprocessor, developed by INTEL Corporation, Santa Clara, Calif. This AT/XT architecture is commonly used by the so-called "Personal Computer," or "PC".

Such single-board computers accept expansion cards, which interface with the system bus 155. Three such cards are shown:

(1) An audio card 160 (such cards are commonly called Digital Signal Processing (DSP) boards);
(2) A data I/O (Input/Output) card 170; and
(3) A video grabber card 180, also called a "frame grabber".

The audio card 160 receives the analog output of the stethoscope pick-up 72 and converts this analog output into digital format. The audio card performs the A/D function indicated in FIG. 6, as well as other functions.

The audio signal produced by the pick-up 72 can also be routed to a separate digitizing apparatus 161, as indicated. This digitizing apparatus shares a connector 163 with the pulse oximeter 104 and the ECG monitor 119, via multiplexer 162. The connector 163 produces digital output indicative of the signals produced by the stethoscope, the pulse oximeter, and the ECG monitor, multiplex fashion, for transmission to a remote site.

The data I/O card 170 receives digital data from the pulse oximeter 104 and the ECG monitor 119, and presents the respective digital signals to the system bus 155. The video grabber card 180 receives the NTSC signal from the CCD camera 3, digitizes the data, and presents it to the system bus 155. The motherboard 190, which contains the microprocessor, stores the data received by the cards 160, 170, and 180, in mass storage 205, or otherwise processes it, as appropriate. The video data, received by the video grabber card 180, can be displayed on the video display 25, by a video driver card 210. In addition, as indicated by line 212, the NTSC analog video signal is delivered directly to a video jack 213.

The data received by all cards 160, 170, and 180 can be transmitted along the common-carrier telephone network by a modem 215. Alternately, an optional cellular modem 225 can be used, which uses a satellite data link, through an antenna 227. The cellular modem can be advantageous in the event of natural disasters, when electric power may be in short supply.

The computer 150 can store an instruction program 230, as indicated, which contains instructions for a technician on how to use the equipment contained within the valise 2. The instructions are shown on the video display 25, and include pictures, drawings, and text, as appropriate.

In addition, the computer can include speakers 240, thereby allowing a multi-media presentation of the instructions. The speakers can be driven by the audio card 160, since many audio digitizing cards contain the ability to convert digital data to analog output. The multi-media presentation, in effect, allows a video-taped presentation of the instructions, using the display 25 for video images, and the speakers 240 for sound.

The use of the computer 150 can simplify data transmission, by storing data, and transmitting it over a longer time than its own duration. For example, if a modem is used, the bandwidth available will be restricted. The restricted bandwidth will not, in general, accomodate high-bandwidth signals, such as those produced by the video camera, or those produced by the stethoscope in certain cases. Such high-bandwidth signals cannot be transmitted in real-time over the restricted-bandwidth modem.

However, once the respective data becomes digitized, it can be stored, and bandwidth limitations, in effect, become converted to time limitations. That is, a large-bandwidth signal produces a large amount of digital data per second, compared with a small-bandwidth signal. The larger amount of digital data merely requires more time to transmit.

This increased time of transmission will not be perceived as significant by medical personnel receiving the signals at a remote location. The highest-bandwidth signal will be that produced by the video camera 3. With suitable compression techniques, which are frames per second can be attained. Each frame can contain 640×480 pixels, with each pixel containing twenty-four bits of color information. Such a video rate approaches full motion video, and is acceptable for many types of medical examination.

Equipment List

The equipment listed below was used for prototype development and shown in FIGS. 2, 6, and 7 is commercially available. The equipment is available from the sources indicated below, and the instruments are normally stored within the cavities or pockets 250 within the valise 2 when the valise is being carried.

| Equiptment | Source |
|---|---|
| Otoscope 20 | Welch-Allyn Skaneateles Falls, NY |
| Ophthalmoscope 30 | Welch-Allyn |
| Video Camera 3 (Model 8280) | Cohu, San Diego, CA |
| Rhino-Laryngoscope 50 (Model ENF-P3) | Olympus America, Irving, TX |
| Fundus Camera 60 (Model RC-2) | Kowa Company, Ltd., Japan |
| Electronic Stethoscope 70 | Andries Tek, Austin, TX |
| Pulse Oximeter 104 (Model Micro $O_2$) | Siemens Med. Electronics, Danvers, MA |
| ECG monitor 119 (Biolog) | Micromedial Industries Northbrook, IL |
| TFT Monitor 25 (Model 9M-60U) | Sharp Electronics Corp. Mahwah, NJ |
| Audio Card 160 | Creative Labs Melpitas, CA |
| Data I/O Card 170 | National Instruments |
| Video Grabber 180 | Play, Inc. Rancho Cordova, VA |
| Single-Board Computer 150 | Adastra Systems, Hayward, CA |
| Macro lens (C6X18G) | Scientific Systems Arlington, TX |

Definitional Matters

"Video": The term "video camera" should not be construed as necessarily requiring full-motion video, such as 30 frames-per-second, or faster. "Video" is a generic term, used to refer to an imaging device which can produce signals suitable for display on a video monitor, such as a television or a computer display. Thus, a "video" camera can take still photographs, full-motion photographs, or ranges of motion between these two.

"Portable." One definition of "portable" is that it can be carried by hand. Another definition of "portable" includes the requirement that the apparatus be transportable as carry-on luggage in standard commercial aircraft.

"Electrocardiogram": One definition is that the electrocardiogram is a "graph," as the name implies, of electrical impulses taken from the skin, at specific locations, and in a specific manner, which represents electrical activity of the heart.

Numerous substitutions and modifications can be undertaken without departing from the true spirit and scope of the invention. What is desired to be secured by Letters Patent is the invention as defined in the following claims.

We claim:
1. Medical diagnostic apparatus, comprising:
   a) a programmable digital computer;
   b) audio means for deriving audio signals usable to a physician from selected internal physiological activity of a subject, and delivering the audio signals to the computer;
   c) video means for deriving visual images from parts of the subject's physiology, and delivering video signals indicative thereof to the computer;
   d) data means for deriving data signals indicative of physiological activity of the subject, and delivering the data signals to the computer; and
   e) means for suppressing receipt of ambient noise by the audio means.
2. Apparatus according to claim 1, and further comprising:
   f) instrumentation means for providing data indicative of
      i) oxygen saturation percentage in blood;
      ii) heart rate;
      iii) electrocardiogram.
      iv) blood pressure; and
      v) temperature.
3. Apparatus according to claim 1, and further comprising
   f) communication means for transmitting said audio signals, video signals, and data signals, via a telephone link, from the computer to a remote location.
4. Apparatus according to claim 1, and further comprising
   f) program means, for running on the computer, which presents instructions for operation of the apparatus.
5. Apparatus according to claim 1, wherein the audio means comprises a stethoscope-microphone combination.
6. Apparatus according to claim 5, wherein the audio means further comprises an otoscope.
7. Apparatus according to claim 1, wherein the audio means comprises a stethoscope.
8. Apparatus according to claim 1, wherein the physiological activity of paragraph (b) includes heart, lung, and intestinal activity.
9. Apparatus according to claim 1, and further comprising:
   h) a pulse oximeter and an electrocardiogram monitor for producing signals for the communication means to transmit to the remote location.
10. Apparatus according to claim 9, and further comprising:
    i) a stethoscope which produces signals for the communication means to transmit to the remote location.
11. A medical diagnostic apparatus, comprising:
    a) a video camera;
    b) an otoscope;
    c) an ophthalmoscope;
    d) a rhino-laryngoscope;
    e) macro lens
    f) mounting means for mounting the otoscope, ophthalmoscope and rhino-laryngoscope to the video camera;
    g) a programmable digital computer;
    h) a frame-grabber card, connected to the computer, for receiving data indicative of video images from the video camera, and converting the data into digital form to the computer;
    i) a stethoscope having a microphone which produces analog signals indicative of sounds which the stethoscope detects;

j) an audio digitizing card, connected to the computer, for receiving the analog signals, and converting them to digital format;

k) a pulse oximeter;

l) an electro-cardiogram (ECG) monitor;

m) blood pressure monitor;

n) temperature monitor;

o) a data input card, connected to the computer, for receiving data from the pulse oximeter and ECG monitor; and p) display means for displaying output of the pulse oximeter, the ECG monitor, and the video camera.

12. Apparatus according to claim 11, q) further comprising a case capable of containing all components listed in paragraphs (a) through (q); and r) in which all components within said case, plus said case itself, are subject to hand-carriage by an average human.

13. Apparatus according to claim 11, and further comprising:

n) program means, for running on said computer, which present instructions as to operation of selected components of the apparatus.

* * * * *